United States Patent [19]
Spiegel

[11] Patent Number: 5,975,904
[45] Date of Patent: *Nov. 2, 1999

[54] ARTICULATED BONE RECONSTRUCTION BAR

[76] Inventor: Jeffrey H. Spiegel, 662 Castro St., San Francisco, Calif. 94114

[ * ] Notice: This patent issued on a continued prosecution application filed under 37 CFR 1.53(d), and is subject to the twenty year patent term provisions of 35 U.S.C. 154(a)(2).

[21] Appl. No.: 08/985,402

[22] Filed: Dec. 5, 1997

[51] Int. Cl.$^6$ ........................................................ A61C 8/00
[52] U.S. Cl. .................................. 433/176; 623/11; 623/16
[58] Field of Search .................................... 623/11, 16, 18, 623/23; 433/172, 173, 175, 176

[56] References Cited

U.S. PATENT DOCUMENTS

| | | | |
|---|---|---|---|
| 4,044,467 | 8/1977 | Linkow et al. | 433/176 |
| 4,225,668 | 9/1980 | Bartoli | 433/176 |
| 4,917,701 | 4/1990 | Morgan | 623/16 |
| 4,990,160 | 2/1991 | Terino | 623/11 |
| 5,052,928 | 10/1991 | Andersson | 433/172 |
| 5,219,286 | 6/1993 | Hader | 433/172 |
| 5,306,150 | 4/1994 | Gittleman | 433/176 X |
| 5,445,650 | 8/1995 | Nealis | 623/18 |
| 5,496,371 | 3/1996 | Eppley et al. | 623/16 |
| 5,580,247 | 12/1996 | Gittleman | 433/176 X |

OTHER PUBLICATIONS

Leibinger brochure for Command Comprehensive Mandibular Fixation System. 6 pages. Aug. 1995.

*Primary Examiner*—Nicholas D. Lucchesi
*Attorney, Agent, or Firm*—Jack Lo

[57] ABSTRACT

An articulated bone reconstruction bar includes a series of short segments connected by fixable axles. The length of the bar is adjusted by varying the number of segments. Before the fixable axles are tightened, the bar is positioned across a discontinuity on a bone. It is adjusted to match the contour of the bone, and the fixable axles are tightened to fixate the connections between the segments and make the bar rigid. The bar is then attached to the bone with mounting screws extending through the segments. Fixable axles with long posts may be used for mounting a dental support plate at the gum line in an area where bone has been lost or removed. If failure occurs, the fixable axles enable the broken segments to be replaced without replacing the entire bar.

17 Claims, 3 Drawing Sheets

ARTICULATED BONE RECONSTRUCTION BAR

BACKGROUND OF THE INVENTION

1. Field of the Invention

This invention relates generally to surgical implants for repairing continuity defects in bones, such as the mandible.

2. Prior Art

Discontinuities in bones, such as the mandible or jaw bone, may comprise of a fracture caused by an accident, or a missing section caused by the surgical removal of a diseased portion. The defects are commonly repaired by attaching a bar of titanium, stainless steel, or other metal alloy, across the fracture or gap. A typical bar includes a series of screw holes and intermediary segments. The bar is attached to the mandible with screws positioned through the holes. However, it must be cut to size and accurately bent to conform to the contour of an individual mandible before installation. Due to the stiffness of the bar and the accuracy required, cutting and bending the bar may take two hours or longer. If the bending is not completely accurate, the mandible is stressed when the bar is tightened thereon, and also deformed to prevent proper dental occlusion. Further, the narrow intermediary segments between the screw holes create stress points, which are exacerbated by bending, where failure sometimes occur. If broken, the entire bar must be surgically removed and replaced, causing further suffering to the patient.

U.S. Pat. No. 4,225,668 to Bartoli shows a dental support bar for mounting dentures. It is comprised of segments connected by pins. Threaded sleeves are screwed onto the pins. Plates attached to the lower end of the pins are embedded in the gum. The segments are disclosed as requiring bending to follow the gum line. The dental support bar cannot be used for repairing discontinuities in a mandible, because the pins are merely attached to the gum, and the pivots between the bar segments are not tightly connected enough to remain rigid, i.e., the bar relies on the mandible for stability. It can only be used on a part of the jaw which is normal, i.e., without a reconstruction bar.

U.S. Pat. No. 5,219,286 to Hader shows another dental support bar for mounting dentures. It is comprised of segments connected by ball-and-socket joints attached to the jaw by posts. The segments arc extendable to allow for unequal spacing between the joints. The support bar thus relies on the jaw for stability, so that it cannot be used for reconstructing a broken jaw. It must also be used in combination with a mandible reconstruction bar when there is a discontinuity in the mandible. It can also only be used on a part of the jaw which is normal.

OBJECTS OF THE INVENTION

Accordingly, objects of the present articulated bone reconstruction bar are:

to repair discontinuities in a bone;
to be easily and quickly adjustable in length without requiring cutting;
to be easily and quickly adjustable to accurately follow the contour of the bone;
to remain rigid in a selected position for stabilizing the bone;
to minimize stress on the bone;
to be easily repairable when broken, without having to replace the entire bar; and
to provide an integrated dental support for mounting dentures where bone has been lost or removed when the bar is applied to a mandible.

Further objects of the present invention will become apparent from a consideration of the drawings and ensuing description.

BRIEF SUMMARY OF THE INVENTION

An articulated bone reconstruction bar includes a series of short segments connected by fixable axles. The length of the bar is adjusted by varying the number of segments. Before the fixable axles are tightened, the bar is positioned across a discontinuity on a bone. It is adjusted to match the contour of the bone, and the fixable axles are tightened to fixate the connections between the segments and make the bar rigid. The bar is then attached to the bone with mounting screws extending through the segments. When the bar is applied to a mandible, fixable axles with long posts may be used for mounting a dental support plate at the gum line in an area where bone has been lost or removed. If failure occurs, the fixable axles enable the broken segments to be replaced without replacing the entire bar.

DRAWING REFERENCE NUMERALS

Figure 1:
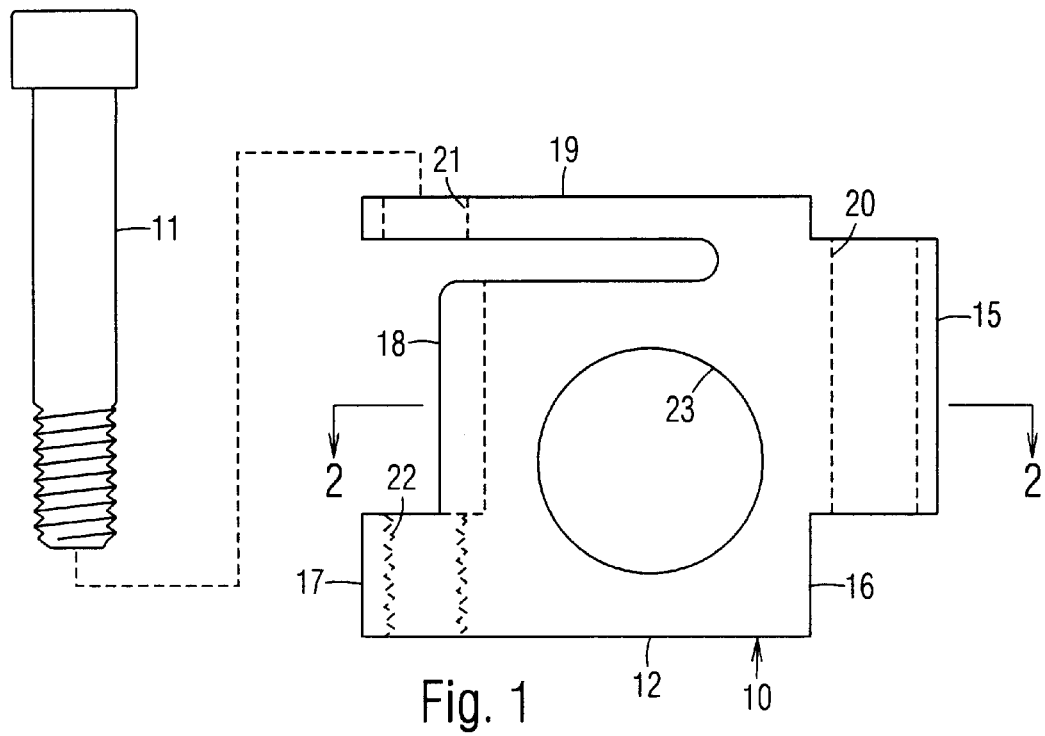
FIG. 1 is a side view of a segment of a first embodiment of the articulated bone reconstruction bar.
Figure 2:
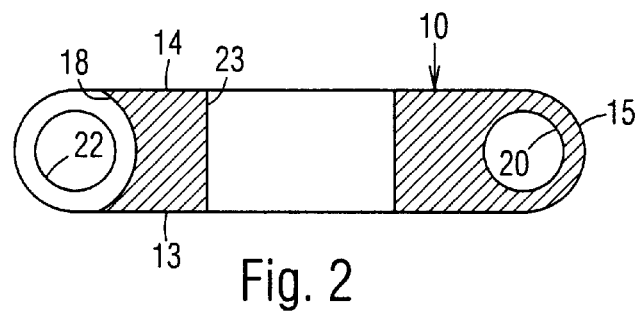
FIG. 2 is a top sectional view of the segment, taken along line 2—2 in FIG. 1.
Figure 3:
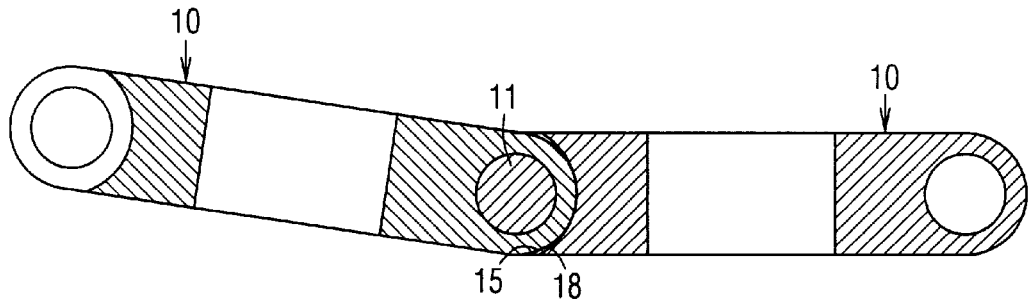
FIG. 3 is a top sectional view of two segments connected together.
Figure 4:
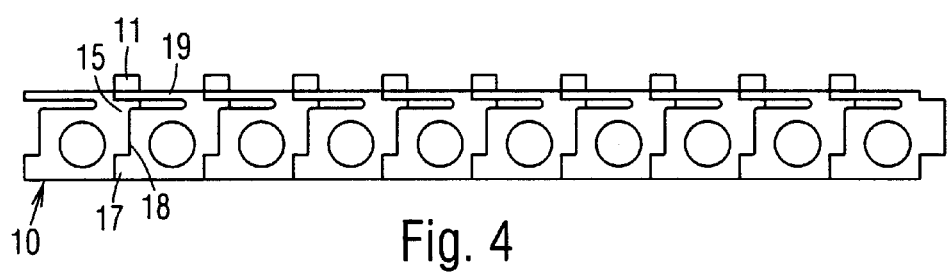
FIG. 4 is a side view of a series of segments connected together.
Figure 5:
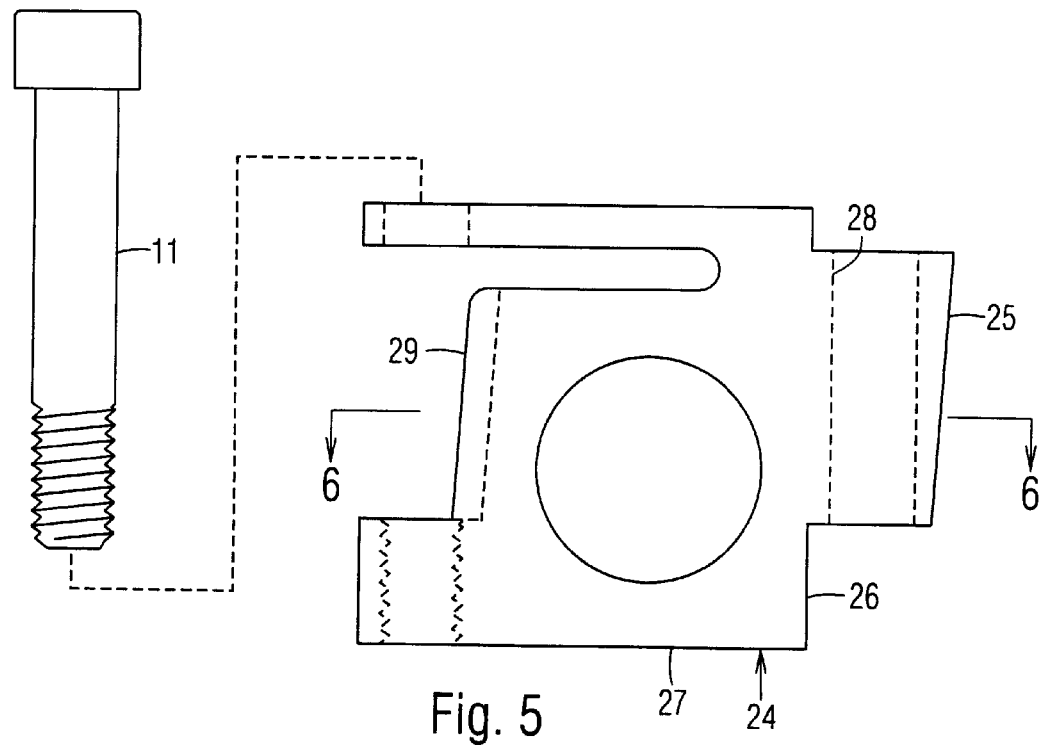
FIG. 5 is a side view of a segment of a second embodiment of the articulated bone reconstruction bar.
Figure 6:
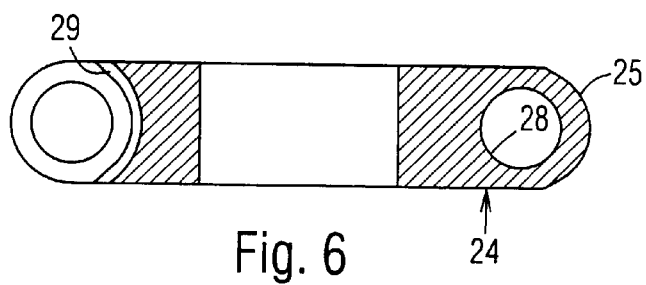
FIG. 6 is a top sectional view of the segment, taken along line 6—6 in FIG. 5.
Figure 7:
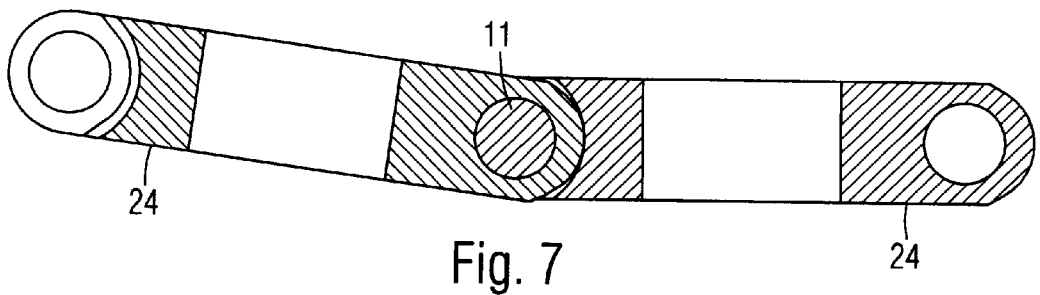
FIG. 7 is a top sectional view of two segments connected together.
Figure 8:
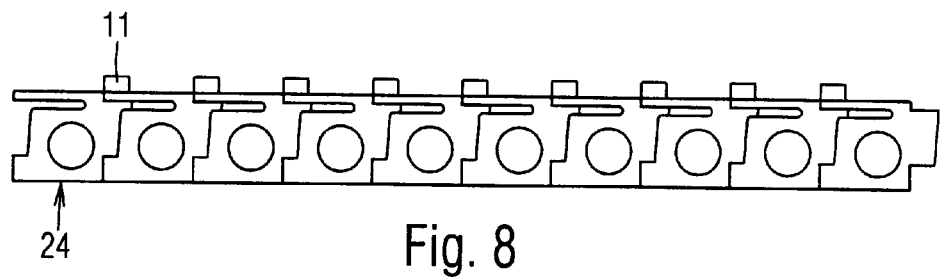
FIG. 8 is a side view of a series of segments connected together.
Figure 9:
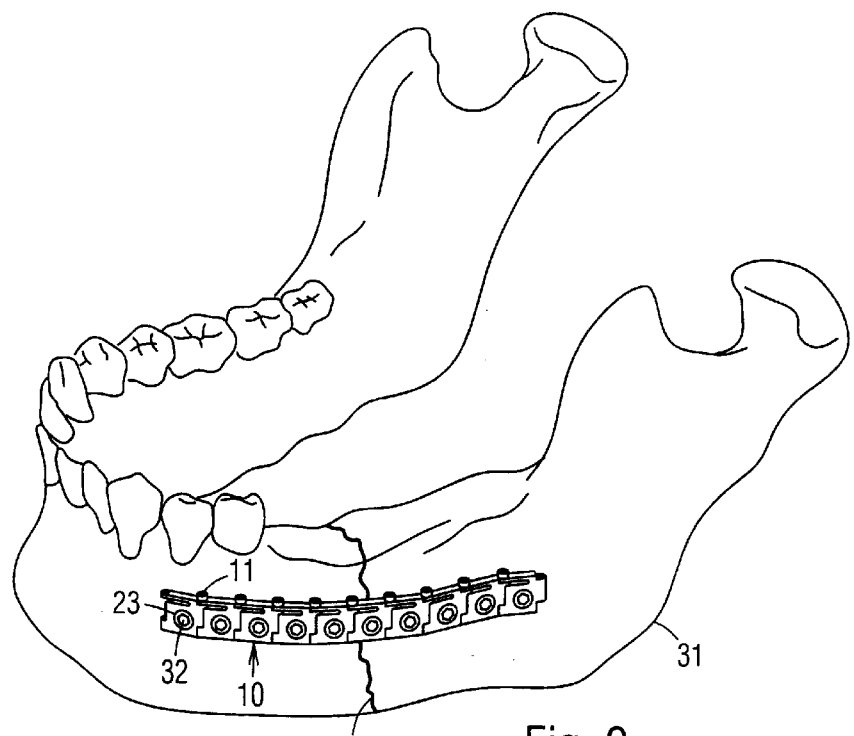
FIG. 9 is a side perspective view of the bar attached to a mandible.
Figure 10:
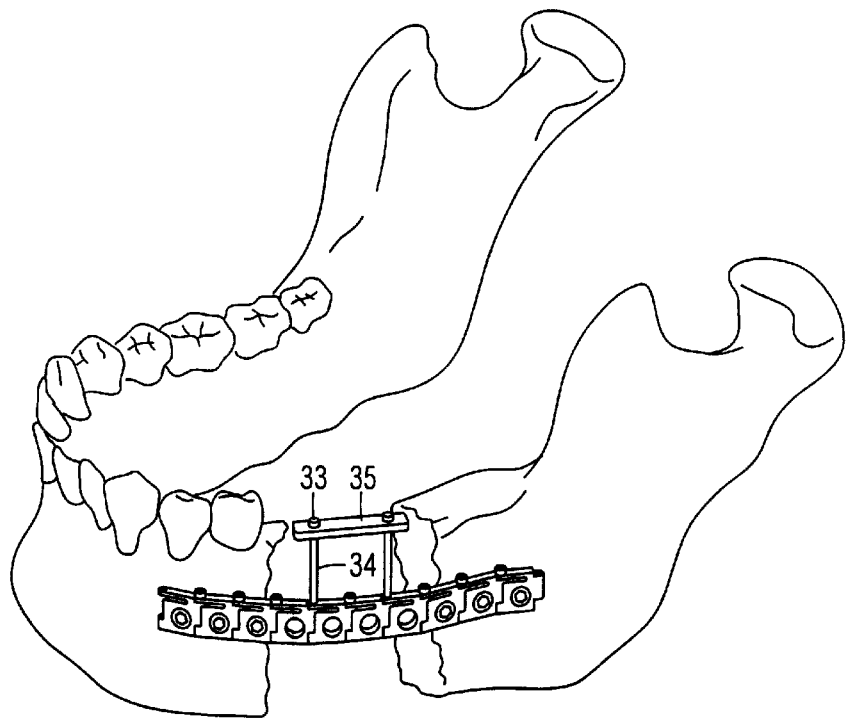
FIG. 10 is a side perspective view of the bar with a dental support plate.
Figure 11:
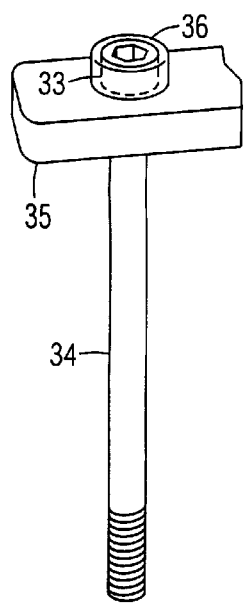
FIG. 11 is a side perspective view of an alternative embodiment of a fixable axle.

| | |
|---|---|
| 10. Segment | 11. Fixable Axles |
| 12. Main Body Member | 13. Side |
| 14. Side | 15. Tab |
| 16. Edge | 17. Tab |
| 18. Edge | 19. Tab |
| 20. Axle Bore | 21. Axle Bore |
| 22. Axle Bore | 23. Mounting Hole |
| 24. Segment | 25. Tab |
| 26. Edge | 27. Main Body Member |
| 28. Bore | 29. Edge |
| 30. Defect | 31. Mandible |
| 32. Mounting Screw | 33. Fixable Axle |
| 34. Posts | 35. Dental Support Plate |
| 36. Antibiotic Gelatin Sleeve | |

DETAILED DESCRIPTION OF THE INVENTION

FIGS. 1–2:

A first embodiment of an articulated bone reconstruction bar is comprised of a series of identical segments 10 (one shown) connected by screws or fixable axles 11 (one shown). Each segment 10 includes a main body member 12 with a flat outer side 13 and a flat inner side 14. A tab 15 projects from a generally intermediate position on a vertical edge 16, and a tab 17 projects from the lower end of an opposite edge 18. A long tab 19 has a proximal end attached to member 12 adjacent edge 16, and a distal end position over tab 17. The edge of tab 15 is rounded convex, and edge 18 is rounded and concave.

A smooth axle bore 20 extends vertically through tab 15. A smooth axle bore 21 extends vertically through the distal end of tab 19, and a threaded axle bore 22 extends through tab 17 in alignment with bore 21 for receiving fixable axle 11, which is threaded only at its distal end. A mounting hole 23 extends through body member 12 orthogonally to the axis of fixable axle 11. The radius of edge 18 is slightly larger than the radius of tab 15, and is also slightly eccentric to the axis of bores 21 and 22.

FIG. 3:

Two segments 10 are shown connected by fixable axle 11. Tab 15 of one segment is in abutting and rotatable engagement with edge 18 of the adjacent segment. The slightly larger radius of edge 18 relative to tab 15 enables the segments to pivot. The larger the difference between the radiuses, the greater the rotation possible between the segments, and vice versa.

FIG. 4:

A series of segments 10 are connected together by positioning tab 15 of each segment against edge 18 of an adjacent segment, and between tab 19 and tab 17. Fixable axles 11 are inserted into the aligned bores between adjacent segments. A bar of any length can be quickly assembled by simply varying the number of segments used.

FIGS. 5–8:

In a second embodiment of the bone reconstruction bar, each segment 24 includes a tab 25 extending from a vertical edge 26 of a main body member 27. Tab 25 has a rounded convex edge which is slightly tapered in a longitudinal direction, thus forming a partial cone. An opposite edge 29 of member 27 is rounded and concave, and is tapered in a longitudinal direction, thus forming a partial funnel. When adjacent segments are tightened by fixable axles 11, tapered tab 25 of one segment is tightly wedged against tapered edge 29 of the next segment, so that the segments are securely fixed in position.

FIG. 9:

After the reconstruction bar is assembled, but before fixable axles 11 are tightened, segments 10 are movable relative to each other, so that the bar is flexible. The bar is positioned across a defect 30 in a bone, such as a mandible 31. Hinged segments 10 enable the bar to be easily and quickly adjusted to conform to mandible 31 with a high degree of accuracy. Fixable axles 11 are tightened to fix segments 10 in their selected positions and make the bar extremely rigid. The bar is attached to mandible 31 with mounting screws 32 extending through mounting holes 23. The high degree of accuracy in contouring achievable with the bar minimizes stress on the mandible, and preserves the shape of the mandible for proper dental occlusion. The discontinuity in the bone is thus repaired. If one or more segments 10 fail, the corresponding fixable axles 11 may be removed and the failed segments replaced, without having to replacing the entire bar.

FIG. 10:

The reconstruction bar is also usable for bridging a missing section in a bone. When the bar is applied to a mandible, fixable axles 33 with elongated posts 34 may be used for connecting some segments in the gap. A dental support plate 35 may be mounted on top of posts 34 for attaching dentures (not shown) in the gap.

FIG. 11:

An antibiotic gelatin sleeve 36 may be provided around the head of fixable axles 33 for preventing infection between axles 33 and body tissue.

SUMMARY AND SCOPE

Accordingly, an articulated bone reconstruction bar is provided for repairing discontinuities in a bone. It is easily and quickly adjustable in length without requiring cutting. It is easily and quickly adjustable to accurately follow the contour of the bone. When tightened, it remains extremely rigid in a selected position for stabilizing the bone. It minimizes stress on the bone when installed. It is easily repairable when broken, without having to replace the entire bar. When it is applied to a mandible, it also provides an integrated dental support for mounting dentures in an area where bone has been lost or removed.

Although the above description is specific, it should not be considered as a limitation on the scope of the invention, but only as an example of the preferred embodiment. Many substitutes and variations are possible within the teachings of the invention. For example, segments 10 may be made of any bio-compatible material, such as titanium or stainless steel. Fixable axles 11 may incorporate locking features for preventing loosening, or lock washers may be used. Fixable axles 11 may be any suitable type of axle which can be tightened. Mounting holes 23 may be notches. The mating surfaces between adjacent segments may be textured for increasing friction and thus the rigidity of the bar. In addition to the mandible, the bar may be used for repairing other bones. Therefore, the scope of the invention should be determined by the appended claims and their legal equivalents, not by the examples given.

We claim:

1. A bone reconstruction bar for repairing a discontinuity in a bone, comprising:

a plurality of pivotable segments arranged in a series;

a mounting hole positioned in each of said segments for receiving a mounting screw attaching said bar to said bone across said discontinuity; and a plurality of fixable axles each connecting a pair of adjacent segments, said segments are easily pivotable relative to each other before said fixable axles are tightened, and said bar is adjustable in shape for closely following a contour of said bone, said segments are fixed relative to each other in selected positions and said bar made extremely rigid by tightening said fixable axles.

2. The bone reconstruction bar of claim 1, further including a dental support plate attached to a top end of at least one of said fixable axles for attaching dentures.

3. The bone reconstruction bar of claim 2, further including an antibiotic gelatin sleeve surrounding said top end of said at least one of said fixable axles for preventing infection.

4. The bone reconstruction bar of claim 1, further including an extended fixable axle with an elongated post extending substantially above a corresponding one of said segments, and a dental support plate attached to a top end of said post for attaching dentures.

5. The bone reconstruction bar of claim 4, further including an antibiotic gelatin sleeve surrounding said top end of said post for preventing infection.

6. A bone reconstruction bar for repairing a discontinuity in a bone, comprising:

a plurality of pivotable segments arranged in a series, each of said segments including a rounded convex edge, and an opposite rounded concave edge, said convex edge and said concave edge of adjacent segments are in abutting and rotatable engagement;

a mounting hole positioned in each of said segments for receiving a mounting screw attaching said bar to said bone across said discontinuity; and a plurality of fixable axles each connecting a pair of said adjacent segments, said segments are easily pivotable relative to each other before said fixable axles are tightened, and said bar is adjustable in shape for closely following a contour of said bone, said segments are fixed relative to each other in selected positions and said bar made extremely rigid by tightening said fixable axles.

7. The bone reconstruction bar of claim 6, wherein said rounded convex edge is tapered in a longitudinal direction thereof forming a partial cone, and said concave edge is tapered in a longitudinal direction thereof forming a partial funnel, said convex edge is tightly wedged against said concave edge when a corresponding one of said fixable axles is tightened.

8. The bone reconstruction bar of claim 6, further including a dental support plate attached to a top end of at least one of said fixable axles for attaching dentures.

9. The bone reconstruction bar of claim 8, further including an antibiotic gelatin sleeve surrounding said top end of said at least one of said fixable axles for preventing infection.

10. The bone reconstruction bar of claim 6, further including an extended fixable axle with an elongated post extending substantially above a corresponding one of said segments, and a dental support plate attached to a top end of said post for attaching dentures.

11. The bone reconstruction bar of claim 10, further including an antibiotic gelatin sleeve surrounding said top end of said post for preventing infection.

12. A bone reconstruction bar for repairing a discontinuity in a bone, comprising:

a plurality of pivotable segments arranged in a series;

a first tab extending from an edge of each of said segments, said first tab having a rounded convex edge;

a pair of spaced apart tabs extending from an opposite edge of each of said segments, said opposite edge having a rounded concave edge, said first tab is positioned between said pair of spaced apart tabs of an adjacent segment, said convex edge and said concave edge of adjacent segments are in abutting and rotatable engagement;

a mounting hole positioned in each of said segments for receiving a mounting screw attaching said bar to said bone across said discontinuity; and a plurality of fixable axles each extending through said first tab and said spaced apart tabs of each pair of adjacent segments, said segments are easily pivotable relative to each other before said fixable axles are tightened, and said bar is adjustable in shape for closely following a contour of said bone, said segments are fixed relative to each other in selected positions and said bar made extremely rigid by tightening said fixable axles.

13. The bone reconstruction bar of claim 12, wherein said rounded convex edge is tapered in a longitudinal direction thereof forming a partial cone, and said concave edge is tapered in a longitudinal direction thereof forming a partial funnel, said convex edge is tightly wedged against said concave edge when a corresponding one of said fixable axles is tightened.

14. The bone reconstruction bar of claim 12, further including a dental support plate attached to a top end of at least one of said fixable axles for attaching dentures.

15. The bone reconstruction bar of claim 14, further including an antibiotic gelatin sleeve surrounding said top end of said at least one of said fixable axles for preventing infection.

16. The bone reconstruction bar of claim 12, further including an extended fixable axle with an elongated post extending substantially above a corresponding one of said segments, and a dental support plate attached to a top end of said post for attaching dentures.

17. The bone reconstruction bar of claim 16, further including an antibiotic gelatin sleeve surrounding said top end of said post for preventing infection.

\* \* \* \* \*